United States Patent
Hotier et al.

(10) Patent No.: US 8,194,245 B2
(45) Date of Patent: Jun. 5, 2012

(54) METHOD FOR ON-LINE MEASUREMENT IN SIMULATED MOVING BED UNITS AND APPLICATION TO CONTROL AND REGULATION OF SAID UNITS

(75) Inventors: Gerard Hotier, Rueil Malmaison (FR); Philibert Leflaive, Mions (FR); Mathieu Digne, Lyons (FR); Philippe Marteau, Paris (FR); Jean-Lucien Molle, Croix (FR); Michel Leclercq, Bois-le-Rol (FR); Sophie Dewally-Morel, Marchiennes (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 0 days.

(21) Appl. No.: 12/907,597

(22) Filed: Oct. 19, 2010

(65) Prior Publication Data
US 2011/0198500 A1    Aug. 18, 2011

Related U.S. Application Data

(63) Continuation of application No. 12/719,491, filed on Mar. 8, 2010, now abandoned.

(30) Foreign Application Priority Data

Mar. 9, 2009   (FR) ..................................... 09 01108

(51) Int. Cl.
*G01J 3/44*    (2006.01)

(52) U.S. Cl. ........................................ 356/301; 356/318
(58) Field of Classification Search ........... 356/301–318
See application file for complete search history.

(56) References Cited

U.S. PATENT DOCUMENTS

| 6,376,734 B1 | 4/2002 | Magne-Drisch et al. |
| 2008/0084555 A1 | 4/2008 | Yoo |

FOREIGN PATENT DOCUMENTS

| DE | 102007043484 A1 | 6/2008 |
| FR | 2795407 A1 | 12/2000 |
| FR | 0901108 R | 9/2009 |

OTHER PUBLICATIONS

Estienne, F. et al. "Multivariate calibration with Raman spectroscopic data: a case study." (Analytica Chimica Acta), Dec. 1, 2000, 185-201.
Marteau, Philippe et al. "Remote Raman spectroscopy for process control." (Vibrational Spectroscopy), Jun. 6, 1994, 101-109, 9:1.

*Primary Examiner* — Tarifur Chowdhury
*Assistant Examiner* — Tara S Pajoohi
(74) *Attorney, Agent, or Firm* — Millen, White, Zelano & Branigan, P.C.

(57) ABSTRACT

The present invention describes a method for measuring the concentrations of species present at one point of a separation unit functioning in simulated moving bed mode (SMB), using an immersing probe located at one point in the unit or on one of the streams entering or leaving said unit, and a thermocouple located in the vicinity of the immersing probe, in which a Raman spectrum obtained using a laser source functioning at a wavelength of 785 nm is utilized.

6 Claims, 1 Drawing Sheet

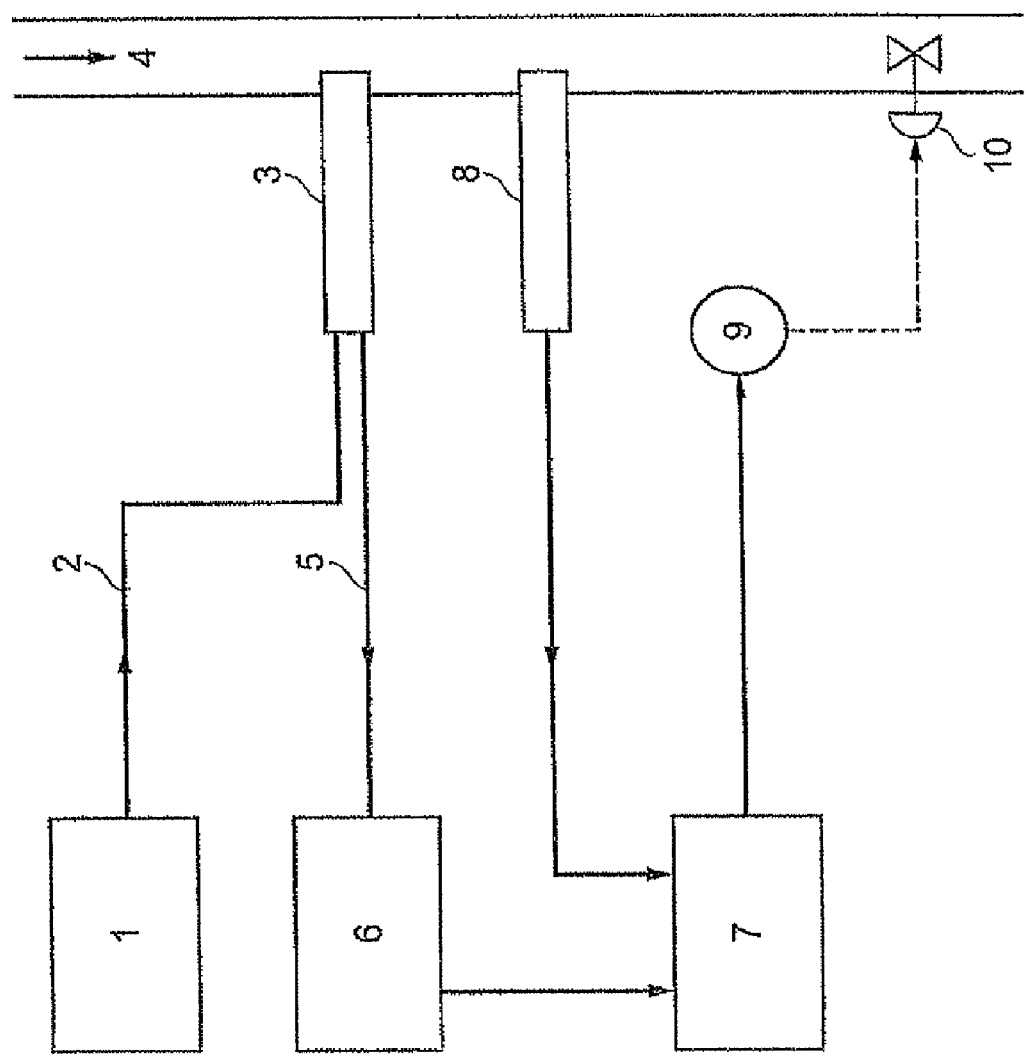

METHOD FOR ON-LINE MEASUREMENT IN SIMULATED MOVING BED UNITS AND APPLICATION TO CONTROL AND REGULATION OF SAID UNITS

This application is a continuation application of U.S. Ser. No. 12/719,491, filed Mar. 8, 2010, now abandoned. This application claims the benefit of priority to France Application No: 0901108, filed Mar. 9, 2009.

FIELD OF THE INVENTION

The present invention relates to the field of on-line measurement methods and devices for controlling and regulating simulated moving bed (hereinafter abbreviated to SMB) units for the separation of xylenes.

More precisely, the present invention pertains to the on-line measurement of the compositions of streams of hydrocarbons moving in the various separation zones of said units. This measurement of the concentrations is obtained from Raman spectra of the stream under consideration, using a specific method for processing said spectra which forms an integral part of the present invention.
A particularly advantageous application of the method of the present invention is the separation of various xylenes, the streams moving in the unit being constituted by a mixture of meta-xylene, ortho-xylene, para-xylene and ethylbenzene with a composition that varies as a function of the point of measurement in the separation unit under consideration.

In the prior art, analyses are carried out in real time by taking samples from streams moving in the unit and placing said streams under conditions corresponding to the spectrometer calibration. This conditioning operation constitutes a major limitation which is not compatible with a direct analysis of the various streams taken from a given point in the separation unit.

The present invention allows an analysis of the streams to be carried out, in particular utilizing Raman spectra, directly and under the operating conditions corresponding to their sampling point in the unit.

Another problem which can be overcome by the present invention is that linked to the presence of fluorescent impurities in the samples which may affect the use of Raman spectra. The choice of a different wavelength range from that which was used in the prior art means that a substantially improved signal-to-noise ratio can be enjoyed.

Finally, the present invention provides for substantially improved accuracy of the measurement compared with the prior art; this improvement is principally due to a combination of 3 factors:
  a) the wavelength of the source, allowing an optimized signal/noise ratio to be obtained;
  b) the calibration method allows spectra to be measured at up to 180° C. and 10 bar; and
  c) the use of an immersion rod allows samples to be obtained directly in situ, suppressing the need for passage through a conditioning chamber.

EXAMINATION OF THE PRIOR ART

U.S. Pat. No. 5,684,580 describes a method comprising the production of a Raman spectrum obtained from a sample and utilizing it in a complex mathematical method with a view to determining the concentration of the various species; the measurement is then used to control and regulate the process. The mathematical method employed is a regression model using neural networks and incorporating a multivariate PLS (partial least square) type statistical analysis and/or a principal component type analysis (PCA).

The experimental spectra are represented by vectors containing the principal components and an error vector to account for the variations which are not explained by the known factors. The method proposed in the cited patent suffers from the disadvantage of requiring a regression for each analysis, which is expensive as regards computation time and renders the speed of the analysis incompatible with very rapid acquisition of experimental spectra.

That method also requires a prior analysis of aberrant values (termed "outlier diagnostics" in that text); the model cannot function with those aberrant values. Finally, no mention is made in that patent of the influence of the temperature of the analyzed fluid, which is necessarily variable, in particular during stop or startup phases.

The aim of the present invention is to propose another method for obtaining the concentrations of the various constituents which accommodates the temperature, and using a matrix inversion method derived from a prior calibration.

Taking the temperature into account in an explicit manner overcomes problems linked to unavoidable variations in said temperature in any industrial process, in particular when the unit is not in a steady state, during which periods the analysis is particularly critical.

The mathematical method used in the present invention is compatible with a very rapid response time allowing a "per second" analysis, i.e. a measurement frequency of the order of 1 Hertz.

French patent FR-92/16034 (U.S. Pat. No. 5,569,808) describes a method and a device for regulating a simulated moving bed separation process processing mixtures of aromatic hydrocarbon isomers containing eight carbon atoms. That patent constitutes the closest prior art for the present invention.

The method described in the cited patent consists of sending a monochromatic signal derived from a laser type source to different points of the SMB separation unit, recovering a diffusion signal corresponding to the Raman effect and processing that recovered signal in a spectrometer which delivers the Raman spectrum corresponding to the signal.

A mathematical method for processing the Raman spectrum allows the concentrations of the various species present at the point in the unit under consideration to be determined.

A comparison of the actual concentration profile (calculated from the Raman spectrum) with a reference profile acting as an index value allows a corrective action for the unit to be defined.

The method of the cited patent suffers from a certain number of limitations described below and which the present invention can overcome.

The exciting wavelength is in the range 400 to 1300 nm (nm is the abbreviation for nanometer, i.e. $10^{-9}$ meter), preferably in the range 420 to 650 nm. The first range is extremely broad and covers all of the wavelengths available for lasers in the 1990s.

The choice of a preferred range of 420 nm to 650 nm suffers from a major disadvantage. In practice, impurities are present in the medium. Such impurities are constituted by compounds containing several condensed aromatic rings (of the anthracene, fluorene type and their derivatives) which are fluorescent at wavelengths in the range 500 to 600 nm. Thus, prior to sending them to the optrode, they must be adsorbed on activated charcoal or activated earth. Thus, in situ analysis is impossible.

Furthermore, despite such precautions, the quantities of fluorescent impurities vary from one unit to another, and the observed background noise may be high. This results in a baseline (above which the intensity of the Raman signal is measured) which is not strictly flat.

It has now been discovered that by changing the wavelength of laser diodes, the fluorescence of impurities based on condensed aromatic rings becomes very low. Thus, it becomes possible to carry out the analysis directly under the operating conditions of the process.

1) Furthermore, by using several distinct sources with a reduced spectral width and having a single program and a single calibration with a single multi-channel detector, it is possible to carry out simultaneous quantification at several analysis points. Surprisingly, the signal/noise ratio at the detector in the novel operating window with a wavelength in the range 750 nm to 800 nm is of the same order as that which could be observed between 514 and 532 nm (prior art), despite attenuation of the signal which is proportional to $1/\lambda^4$.

2) Processes for separating C8 aromatic hydrocarbon isomers using simulated moving bed techniques have developed. In particular, advances have been made in distribution plate and molecular sieve technology. It is now possible to separate high purity para-xylene with a smaller number of beds and using a single adsorber instead of 2. In order to regulate the process, it thus becomes sufficient to analyze the streams at one point located in an internal separation zone.

It is no longer vital to carry out an analysis of the streams at least 2 points located in the internal separation zones.

Further, since purely binary separations are rare, it is particularly advantageous to use a single program for quantification allowing a fundamental analysis of the three isomers, ortho-, meta- and para-xylenes, and of ethylbenzene, as well as of the desorbent, generally toluene or para-diethylbenzene or any other potential desorbent, to be carried out.

3) Another problem which has not been solved in the prior art is that of temperature monitoring—Raman spectra are sensitive to this operating variable. In fact, since the temperature is not strictly constant in industrial processes, in particular during stop and startup phases, carrying out the invention of French patent FR-2 699 917 requires taking a small stream of product from one of the principal units of the separation process to process it with a view to partially adsorbing the fluorescent impurities, then cooling it to a controlled temperature before sending it through a cell provided with a window for analysis therein.

According to FR-2 699 917, the concentrations are computed at the analysis temperature, which must therefore be equal to the calibration temperature.

According to the present invention, the use of a novel method for analysis based on the simultaneous measurement of the Raman spectrum and the temperature of the sample at the point of measurement overcomes this problem, provided that a temperature and pressure calibration are carried out (for example at several temperatures between 100° C. and 180° C. at 10 bars (1 bar=$10^5$ pascal)), and provided that a signal processing method is available which accommodates molecular interactions, in particular explicitly takes into account the variation in the effective cross sections of the various species as a function of their concentration.

Finally, at the start of the 1990s, only high power gas lasers (514 nm) were suitable for the envisaged applications to Raman spectrometry. The disadvantages of such gas lasers were their bulk, the need for water to cool the head and their high electricity consumption. An optical beam splitting system was mounted in front of the laser head to distribute the beam to each of the various measuring points.

At the end of the 1990s, solid state lasers appeared (DPSS, diode-pumped solid-state) which operated at 532 nm, with spectral characteristics that are compatible with Raman spectroscopy. Installing them in the measuring heads themselves and their electricity supply meant that they had to be used in flameproof cabinets.

Now, powerful solid state lasers can be installed in the quality control laboratory and the light source can be guided by fibre optics, which means that they have low bulk, have a reduced electricity consumption, and a single laser per measurement point can be used. If it breaks down, only one measurement point is involved; the other measuring points continue to function, and thus maintenance is reduced.

BRIEF DESCRIPTION OF FIG. 1

FIG. 1 is a diagrammatic view of the measuring line comprising the laser source, the spectrometer, the immersing probe and a control and regulation loop which means that the Raman spectrum can be used to define a corrective action for the unit, if necessary.

A laser source 1 emits a beam at 785 nm. This beam is guided along a fibre optic 2 to an immersing probe 3. This immersing probe is immersed into a measuring point of the xylenes separation unit 4 where the concentration of the various constituents is to be determined.

The Raman signal emitted at the measuring point is collected by the immersing probe, then transmitted using a second fibre optic 5 to the Raman spectrometer 6. This latter generates the Raman spectrum corresponding to the measuring point. This spectrum is sent to the PC analyzer 7.

At the same time, in a zone close to the measuring point, a thermocouple 8 is immersed in the unit which can transmit the temperature of the zone under consideration (which thus contains the measuring point for the Raman spectrum) to the PC analyzer 7.

The PC analyzer uses the Raman spectrum and the temperature to determine the concentration of the various species present at the measuring point using the processing method which forms an integral part of the invention. By comparing the concentration values thus obtained with reference concentration values, an actuator 9 is used to act on one or more operating variables of the process, for example the flow rate of a valve, as shown in dotted lines at 10.

The dotted line signifies that it is an optional element in the present measuring line.

BRIEF DESCRIPTION OF THE INVENTION

The present invention describes a method for measuring the concentrations of species present at one point of a separation unit functioning in simulated moving bed mode (SMB), using an immersing probe located at one point in the unit under consideration, termed the measuring point, or on one of the streams entering or leaving said unit, and a thermocouple located in the vicinity of the immersing probe, in order to capture the temperature ($T_{spl}$) of the measuring point, in which method:

a) a monochromatic signal is sent through a first fibre optic connected to the immersing probe, originating from a laser source the wavelength of which is 785 nm plus or minus 1 nm;

b) a signal corresponding to the Raman effect, termed the Raman signal, is captured which re-crosses the immersing probe and passes into a second fibre optic connected to the spectrometer;

c) the Raman spectrum of the signal under consideration is recovered at the spectrometer outlet;

d) the Raman spectrum obtained is processed using a mathematical method which accommodates the temperature ($T_{spl}$) of the measuring point in order to obtain the concentration of the species present at the measuring point under consideration.

In a variation of the invention in which the present measurement method is used to carry out control and regulation of the unit, as a function of the difference between the measured value or values of the concentrations of C8 aromatics and one or more reference values, at least one actuation variable is acted on selected from the following variables: internal flow rates or feed, eluent or extract flow rates, or the permutation period.

Preferably, the cumulative total length of the first fibre optic and the second fibre optic is less than 1000 m, preferably less than 700 m.

The method for obtaining the concentrations $C_j$ used in step d) is based on the formula:

$$C_j = \frac{P_j(T, C_1, \ldots, C_5)\sigma_j(T, C_1, \ldots, C_5)}{\sum_{i=1}^{5} P_i(T, C_1, \ldots, C_5)\sigma_i(T, C_1, \ldots, C_5)}$$

in which:

$P_i$ is the integrated intensity of the Raman band due to molecule i and $\sigma_i$ is the inverse of the relative effective cross section of the molecule i, in which expression the integrated intensities $P_i$ are obtained from the measured intensities $M_j$ on the Raman spectrum using a matrix product in which the coefficients $a_{ij}$ of the matrix M result from a calibration carried out at the temperature ($T_{spl}$) of the measuring point, or at a plurality of temperatures framing said temperature of the measuring point;

$\sigma_i$ denotes the inverse of the relative effective cross section of the molecule i;

in which expression the integrated intensities $P_i$ are obtained from the measured intensities $M_j$ on the Raman spectrum using a matrix product in which the coefficients of the matrix M result from a calibration carried out at the temperature ($T_{spl}$) of the measuring point, or at a plurality of temperatures framing said temperature of the measuring point, the inverse of the effective cross sections $\sigma_i$ being a function of temperature (T) and the concentrations ($C_i$) of the various constituents.

Preferably, the spectrometer uses filters defining a cutoff threshold. As an example, these filters can provide a cutoff above or below a threshold energy. They are known as edge filters.

Preferably, the total length of the first fibre optic and the second fibre optic is less than 1000 m, more preferably less than 700 m.

The measuring method of the present invention can be applied to one or more measuring points distributed over the unit. The unit is a simulated moving bed (SMB) separation unit supplied by a feed containing xylenes and ethylbenzene and producing a raffinate and an extract.

Since the unit is a unit for separating xylenes by SMB, when there is a single measuring point on the unit, this is preferably located at the recycling pumps on the recycling circuit in order to be able to reconstruct the internal concentration profile which is translated in front of this point.

When there are two measuring points on the unit, the first is preferably located in the vicinity of the recycling pump on the recycling circuit, and the second is preferably located in the vicinity of the feed pump on the feed circuit.

When there are three measuring points on the unit, the first point is preferably located in the vicinity of the recycling pump on the recycling circuit, the second point is preferably located near the feed pump on the feed circuit, and the third measuring point is preferably located in the rectification zone of the raffinate distillation column.

The measuring method of the invention may be applied to controlling and regulating a SMB xylenes separation unit, the difference between a concentration profile measured by the present method and a reference concentration profile (corresponding to at least one of the constituents present in the unit) allowing at least one of the control parameters selected from the group constituted by: internal flow rates, the feed flow rate, the eluent flow rate, the extract flow rate, and the permutation period to be acted upon.

DETAILED DESCRIPTION OF THE INVENTION

The present invention can be described as a method for continuously measuring the concentrations of the various species present at a given point in a simulated moving bed separation unit. The principal application of the method is the separation of xylenes using a simulated moving bed (SMB) and so the remainder of the text will use this application to illustrate the possibilities of the invention, but it is applicable to other separations of organic compounds such as the separation of normal or n-paraffins, for example.

From the many pieces of equipment available on the market, extended cavity diode lasers emitting at 785 nm were selected for their compatibility with their use in Raman spectroscopy.

The Raman spectrometer used in the context of the invention is a dispersive Raman spectrometer provided with a toroidal input mirror, improving the quality of the image at the detector by correcting optical aberration, in particular astigmatism. Our application currently uses 3 pathways (6 fibres), but because of the quality of the spectrograph, it would be possible if necessary to substantially increase this number of pathways, for example and preferably by using 3 to 6 pathways.

A particular point of the spectrometer concerns the nature of the rejection filters used to cut off the Rayleigh line. Experience has shown us that filters which cut off within a range (notch filters) change over time: they age, lose their original specifications at varying rates as a function of the external conditions (in particular temperature and humidity).

Advances have provided the market with filters which can cut off above or below an energy threshold (edge filters) which have better characteristics as regards their use in Raman spectroscopy. These improved characteristics concern the energy corresponding to the cutoff threshold, the density, and very low ripple), while retaining their original characteristics of insensitivity to temperature and humidity.

Changes to filters have meant that the only remaining disadvantage of edge type filters compared with notch type filters is the impossibility of visualizing anti-Stokes lines (see definition below).

The edge filter is a high pass filter and a notch filter is a bandpass filter. In our application, the spectral portion located below a cutoff threshold termed the "anti-Stokes" portion is not used and so using an edge filter is completely unaffected by this fact.

The wavelength λ of the incident excitation laser has a major effect on the spectral background and thus substantially modifies the appearance of the Raman spectrum obtained. The choice of optimized wavelength depends on several criteria and often results from a compromise. Firstly, since the Raman signal is weak and its intensity is proportional to $1/\lambda^4$, low wavelength lasers theoretically produce an increase in the signal.

As an example, a 532 nm laser provides a signal which is 5 times more intense that a 785 nm laser. However, this argument is no longer valid for exported measurements. The signal has to be sent through fibre optics which are usually silica-based.

Such fibres cause attenuation the value of which principally depends on the length (L) of the fibre and the wavelength of the signal. Transmission is given by: $T(\%)=10^X$, X being defined by: $X=(-A(\lambda) L/10)$, in which expression:

L is the length of the fibre (in km); and $A(\lambda)$ is the attenuation coefficient (in dB/km).

For standard silica fibres, the attenuation coefficient decreases with wavelength. This property favours the use of long wavelength lasers.

As an example, assuming that a fibre optic has a length L=1 km, the attenuation for a wavelength of 532 nm, A (532 nm), is 13 dB/km, and with a wavelength of 785 nm, the attenuation A (785) nm is 4 dB/km.

The recovered Raman signal will have an intensity which is close for the two incident laser beams. As a consequence, for exported measurements, using lasers in the visible region (532 nm) does not result in a significant increase in the Raman signal compared with lasers in the near infrared (785 nm).

Finally, using a laser in the near infrared (785 nm) induces another advantage compared with a visible laser (532 nm). Dispersive Raman spectrometers use diffraction gratings to disperse the spectral signal as a function of energy.

However, the dispersion in terms of wave number ($cm^{-1}/mm$) is better at 785 nm than at 532 nm.

Hence, by changing from a visible laser to a near infrared laser and by using a diffraction grating with a smaller number of lines (which avoids too high a working angle and thus too low a luminosity), it is possible to retain the same definition for the lines (i.e. an equivalent number of pixels describing the Raman lines).

Furthermore, in order to measure the concentrations of C8-C10 aromatic molecules, the spectral zone of greatest interest (i.e. that with the most characteristics bands) is limited to between 720 and 900 $cm^{-1}$. By changing from a 532 nm laser to a 785 nm laser and selecting another grating optimized for the near infrared, this spectral zone can still be used under the same conditions as before.

In conclusion, changing from a visible laser (532 nm) to a near infrared laser (785 nm) means that problems with fluorescence can be overcome and an equivalent resolution can be obtained, without significantly reducing the intensity of the Raman signal obtained. These elements allow a more accurate and more robust measurement of the concentrations to be made.

The immersing probe can focus the laser beam on the sample, via lenses, and collect the emitted Raman signal.

The immersing probe is a cylindrically shaped steel tube connected to two fibre optics, the out fibre (or first fibre) which guides the signal from the laser source to the measuring point, and the return fibre (or second fibre) which guides the Raman signal from the measuring point to the spectrometer.

The immersed end of the probe (hence its designation as an immersing probe) is constituted by a window, generally formed from sapphire, which allows light to pass.

This end is immersed directly in the medium to be analyzed, meaning that in situ analysis can be carried out without the need for a bypass loop. The immersing probe or probes may be located at different points of the unit depending on the intended aim:

if it is to monitor the unit from the point of view of operational stability, one or more immersing probes may be located in the lines connecting the adsorption beds downstream of the pumps. The aim is then to obtain a concentration profile of the species at a given point in the unit;

it is also possible to place one or more immersing probes inside an adsorption bed. In this case, since the concentration profiles of each of the species are dislocated, a time corresponding to one period of the cycle must pass before a value which can be compared with the preceding value can be regained. If, as an example, a unit with 24 beds has a permutation period of 75 s, then the period of one cycle is 30 minutes;

it may also concern carrying out a measurement of the concentration of the inlet feed or of the raffinate and/or extract output products. In this case, the measuring points will be located either in the supply line or on the raffinate or extract production-lines, generally downstream of the distillation units which separate the raffinate from the desorbent or the extract from the desorbent.

Close to the point of the unit where the Raman spectrum is measured, a thermocouple is installed in order to simultaneously capture the Raman spectrum of the sample zone and its temperature. The term "close" means a distance between the immersed end of the probe and the thermocouple of at most 30 cm.

In the remainder of the text, for simplification the term "measuring point" is used knowing that there may be one or more distributed at various points of the unit. Each measuring point is associated with a thermocouple located in the vicinity of said measuring point in order to measure the temperature of the fluid moving in said vicinity.

The two data (Raman spectrum and temperature) are sent to a PC controlling the analytical line for processing.

The relative concentrations of the various constituents of the mixture are obtained by measuring the Raman spectrum and the temperature using the following processing method. In the case of a sample with five constituents (ortho-, meta-, para-xylene, ethylbenzene and toluene or para-diethylbenzene), the relative concentration of species j, $C_j$, is given by the following relationship, with ($T_{spl}$) being the temperature of the sample:

$$C_j = \frac{P_j(T_{spl}, C_1, \ldots, C_5)\sigma_j(T_{spl}, C_1, \ldots, C_5)}{\sum_{i=1}^{5} P_i(T_{spl}, C_1, \ldots, C_5)\sigma_i(T_{spl}, C_1, \ldots, C_5)} \quad (1)$$

in which expression:

$P_i$ is the integrated intensity of the Raman band due to molecule i; and $\sigma_i$ is the inverse of the relative effective cross section of the molecule i, (by convention, the relative cross section of the solvent is taken to be 1, i.e. $\sigma_{toluene}=\sigma_{paradiethylbenzene}=\sigma_1=1$);

$P_j$ is the integrated intensity of the Raman band of molecule j;

$\sigma_j$ denotes the inverse of the relative effective cross section of the molecule i.

The distinction between the indices i and j is simply a notational convenience; i represents the current index in the summation and j indicates the index of the molecule under consideration.

The denominator represents the summation of the products $P_i \sigma_i$ over the set of constituents i present in the mixture. In general, the values of $P_i$ and $\sigma_i$ depend on both the temperature of the sample $T_{spl}$ and the relative concentrations of the various constituents $C_i$.

The calibration method described below is intended to determine the numerical values of $P_j$ and $\sigma_j$.

Determination of Integrated Intensities $P_i$ at Calibration Temperature $T_{cal}$ For a given temperature, the method for exploiting Raman spectra uses a matrix M termed the transfer matrix which can link the integrated intensity measured on the Raman spectrum obtained at the calibration temperature ($T_{cal}$), $M_j$, to the integrated intensity of the Raman band of constituent j, $P_j$, in accordance with the matrix product $M \cdot P_j = M_j$.

Denoting $a_{ij}$ as the generic element of the transfer matrix M (by construction, $a_{ij}=1$), the following relationship is obtained:

$$\begin{bmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{bmatrix} \begin{bmatrix} P_1 \\ P_2 \\ P_3 \\ P_4 \\ P_5 \end{bmatrix} = \begin{bmatrix} M_1 \\ M_2 \\ M_3 \\ M_4 \\ M_5 \end{bmatrix} \quad (2)$$

The inverse matrix $M^{-1}$ can thus allow the integrated intensities of the Raman band of the constituent j, $P_j$, to be obtained as a linear combination of the measured intensities $M_i$ for each species i. In practice, the values of $a_{ij}$ are obtained from the Raman spectra of the pure constituents measured at the calibration temperature $T_{cal}$, which derives from the assumption that the values of $P_i$ do not depend on the concentration of the other constituents. This approximation is no longer valid in the case of para-xylene and para-diethylbenzene. In fact, the Raman bands for para-xylene and para-diethylbenzene overlap to such a great extent that their respective coefficients in the transfer matrix have to be determined as a function of their concentration. To this end, the Raman spectra of binary mixtures of each of these two constituents with meta-xylene at different concentrations are used.

Determination of the Inverse of the Relative Effective Cross Sections $\sigma_j$ at the Calibration Temperature $T_{cal}$ The inverse of the relative effective cross section $\sigma_j$ of species j is defined as a linear combination of the concentrations of the other constituents weighted by the coefficients $A_{ij}$:

$$\sigma_j = A_{j1}C_1 + A_{j2}C_2 + A_{j3}C_3 + A_{j4}C_4 + A_{j5}C_5 \quad (3)$$

Determination of the values of $A_{ij}$ is carried out by a calibration using a series of five synthesized samples. Each sample is a mixture with a given composition of 5 constituents present in the feed to be treated: ortho- (OX), meta- (MX), and para-xylene (PX) to which ethylbenzene (EB) is added along with the solvent which may be toluene or para-diethylbenzene (PDEB), as in the present illustration.

It will be recalled that by convention, the effective cross section of the solvent is equal to 1, i.e. $\sigma_1 = 1$.

The concentrations of the mixtures corresponding to each of the five samples (expressed as a percentage by weight) are defined in the table below.

| Sample no | % PDEB | % MX | % PX | % OX | % Et |
|---|---|---|---|---|---|
| #1 | 10 | 15 | 20 | 25 | 30 |
| #2 | 15 | 20 | 25 | 30 | 10 |
| #3 | 20 | 25 | 30 | 10 | 15 |
| #4 | 25 | 30 | 10 | 15 | 20 |
| #5 | 30 | 10 | 15 | 20 | 25 |

For each sample, the Raman spectrum is measured at the calibration temperature $T_{cal}$.

The values for the integrated intensities for each constituent $P_i$ are determined from the Raman spectra starting from the transfer matrix M using the procedure indicated above. The concentrations of the constituents are known for each sample and so equation (1) is used to determine the inverse of the effective cross sections $\sigma_j$ which become the unknowns in equation (1).

For sample x (x=1, ... 5), the four equations linking the inverse of the effective cross sections $\sigma_j^x$ at integrated intensities $P_j^x$ and at concentrations $C_j^x$ are:

$$\sigma_2^x P_2^x \left[1 - \frac{1}{C_2^x}\right] + \sigma_3^x P_3^x + \sigma_4^x P_4^x + \sigma_5^x P_5^x = -P_1^x \quad (4)$$

$$\sigma_2^x P_2^x + \sigma_3^x P_3^x \left[1 - \frac{1}{C_3^x}\right] + \sigma_4^x P_4^x + \sigma_5^x P_5^x = -P_1^x$$

$$\sigma_2^x P_2^x + \sigma_3^x P_3^x + \sigma_4^x P_4^x \left[1 - \frac{1}{C_4^x}\right] + \sigma_5^x P_5^x = -P_1^x$$

$$\sigma_2^x P_2^x + \sigma_3^x P_3^x + \sigma_4^x P_4^x + \sigma_5^x P_5^x \left[1 - \frac{1}{C_5^x}\right] = -P_1^x$$

These equations are equivalent to the atria expression:

$$\begin{bmatrix} \sigma_2^x \\ \sigma_3^x \\ \sigma_4^x \\ \sigma_5^x \end{bmatrix} = \quad (5)$$

$$\begin{bmatrix} \left[1 - \frac{1}{C_2^x}\right]P_2^x & P_3^x & P_4^x & P_5^x \\ P_2^x & \left[1 - \frac{1}{C_3^x}\right]P_3^x & P_4^x & P_5^x \\ P_2^x & P_3^x & \left[1 - \frac{1}{C_4^x}\right]P_4^x & P_5^x \\ P_2^x & P_3^x & P_4^x & \left[1 - \frac{1}{C_5^x}\right]P_5^x \end{bmatrix}^{-1} \begin{bmatrix} -P_1^x \\ -P_1^x \\ -P_1^x \\ -P_1^x \end{bmatrix}$$

By writing that equation (1) is verified for each of mixtures x (x=1, ..., 5), for constituent 2, for example, the following system of equations is obtained:

$$A_{21}C_1^1 + A_{22}C_2^1 + A_{23}C_3^1 + A_{24}C_4^1 + A_{25}C_5^1 = \sigma_2^1$$

$$A_{21}C_1^2 + A_{22}C_2^2 + A_{23}C_3^2 + A_{24}C_4^2 + A_{25}C_5^2 = \sigma_2^2$$

$$A_{21}C_1^3 + A_{22}C_2^3 + A_{23}C_3^3 + A_{24}C_4^3 + A_{25}C_5^3 = \sigma_2^3$$

$$A_{21}C_1^4 + A_{22}C_2^4 + A_{23}C_3^4 + A_{24}C_4^4 + A_{25}C_5^4 = \sigma_2^4$$

$$A_{21}C_1^5 + A_{22}C_2^5 + A_{23}C_3^5 + A_{24}C_4^5 + A_{25}C_5^5 = \sigma_2^5 \quad (6)$$

The coefficients $A_{2j}$ are thus obtained by the following matrix equation:

$$\begin{bmatrix} A_{21} \\ A_{22} \\ A_{23} \\ A_{24} \\ A_{25} \end{bmatrix} = \begin{bmatrix} C_1^1 & C_2^1 & C_3^1 & C_4^1 & C_5^1 \\ C_1^2 & C_2^2 & C_3^2 & C_4^2 & C_5^2 \\ C_1^3 & C_2^3 & C_3^3 & C_4^3 & C_5^3 \\ C_1^4 & C_2^4 & C_3^4 & C_4^4 & C_5^4 \\ C_1^5 & C_2^5 & C_3^5 & C_4^5 & C_5^5 \end{bmatrix}^{-1} \begin{bmatrix} \sigma_2^1 \\ \sigma_2^2 \\ \sigma_2^3 \\ \sigma_2^4 \\ \sigma_2^5 \end{bmatrix} \quad (7)$$

Similar expressions are obtained for constituents 3, 4 and 5. Thus, the set of values for $A_{ij}$ for the calibration temperature $T_{cal}$ is obtained and stored following calibration.

Accommodating the Effect of Temperature on Calibration

The temperature is taken into account when determining the concentrations as follows:

The procedures described above (determination of $P_i$ and $\sigma_i$) were carried out for a fixed calibration temperature $T_{cal}$. They were reproduced for several calibration temperatures (a minimum of three temperatures: $T_{cal}^1$, $T_{cal}^2$, $T_{cal}^3$, ...) in order to cover the temperature range of the process, typically 100° C. to 180° C.

For each temperature, a set of 69 coefficients is obtained, corresponding to the frequency of the Raman bands, the contribution to the base line due to each constituent, the elements of the transfer matrix M and their corrections as a function of the concentrations and the values of the coefficients $A_{ij}$, allowing the inverse of the relative effective cross sections to be computed.

The variation in each of these coefficients with temperature is represented by a second order polynomial. The three coefficients of the polynomial are determined by regression over the data obtained for the different calibration temperatures $T_{cal}^1$, $T_{cal}^2$, $T_{cal}^3$.

Thus, for a sample temperature at the measuring point, $T_{spl}$, which is a priori different from the calibration temperatures, the value for the various coefficients at this temperature $T_{spl}$ is obtained.

When the Raman spectrum of a sample with unknown concentration, measured at temperature $T_{spl}$, is recorded, approximate values for $\sigma_1$ (respectively $1//1.11//0.86//0.79$ and $2.70$) are used to calculated the approximate values of concentrations $C_j$ using equation (1). These values arise from measurements carried out on equimolar mixtures of the various constituents with para-diethylbenzene. By default, it is also possible to take all values of $\sigma_i$ as being equal to 1.

Next, these concentrations are used to compute more accurate values for $\sigma_i$ using equation (3). The computation is repeated in an iterative manner until converging values for the concentrations Ci are obtained. Three iterations are generally sufficient to obtain a convergence of the concentrations of less than 0.01%. A typical case of convergence is developed in Table 1.

TABLE 1

Example of iterations for the concentration computation (K = number of iterations and $\Delta_j = C_{j\,msrd} - C_{j\,actual}$)

| | PDEB | MX | PX | OX | Et |
|---|---|---|---|---|---|
| | | $\sigma_j$ (a.u.) | | | |
| K = 0 | 1 | 1 | 1 | 1 | 1 |
| K = 1 | 1 | 1.1106 | 0.8648 | 0.7262 | 2.6788 |
| K = 2 | 1 | 1.1025 | 0.8659 | 0.7290 | 2.6882 |

TABLE 1-continued

Example of iterations for the concentration computation (K = number of iterations and $\Delta_j = C_{j\,msrd} - C_{j\,actual}$)

| | PDEB | MX | PX | OX | Et |
|---|---|---|---|---|---|
| K = 3 | 1 | 1.1024 | 0.8659 | 0.7292 | 2.6882 |
| K = 4 | 1 | 1.1024 | 0.8659 | 0.7292 | 2.6882 |
| | | Raman measurements $C_j$ (%) | | | |
| K = 0 | 15.32 | 28.59 | 29.97 | 19.95 | 6.14 |
| K = 1 | 14.75 | 30.56 | 24.94 | 13.94 | 15.79 |
| K = 2 | 14.76 | 30.36 | 25.00 | 14.00 | 15.86 |
| K = 3 | 14.76 | 30.36 | 24.99 | 14.01 | 15.86 |
| K = 4 | 14.76 | 30.36 | 24.99 | 14.01 | 15.86 |
| actual $C_j$ values | 14.82 | 30.11 | 25.03 | 14.18 | 15.85 |
| | | Differences $\Delta_j$ (%) | | | |
| K = 0 | −0.50 | −1.52 | 4.94 | 5.77 | −9.81 |
| K = 1 | −0.07 | 0.45 | −0.09 | −0.24 | −0.06 |
| K = 2 | −0.06 | 0.25 | −0.03 | −0.18 | 0.01 |
| K = 3 | −0.06 | 0.25 | −0.04 | −0.17 | 0.01 |
| K = 4 | −0.06 | 0.25 | −0.04 | −0.17 | 0.01 |

In summary, starting from the calibration procedure, the on-line measurement of the Raman spectrum and the temperature ($T_{spl}$) in the vicinity of the measuring point, values for $P_i$ and $\sigma_i$ as well as the concentrations $C_i$ of the various constituents are determined.

The method of the invention may be used in particular to determine the concentration profiles of isomers during separation in processes for separating para-xylene or any other isomer (meta-xylene, ortho-xylene and ethylbenzene) from a mixture of aromatic C8 hydrocarbons, possibly diluted in a solvent such as toluene or para-diethylbenzene.

To this end, the Raman spectrum is recorded and the temperature is measured at least one measuring point located on the circuit for moving simulated moving bed fluids (typically but not exhaustively in the lines that connect the adsorbers downstream of the pumps located on these lines).

Inside the adsorbers, once dynamic equilibrium is reached, a concentration profile of ethylbenzene, para-xylene, meta-xylene, ortho-xylene and desorbent (toluene or para-diethylbenzene) is formed. This profile is dislocated inside the adsorbers at a constant rate. One complete cycle is required to return to exactly the original position. As an example, for a 24 bed adsorber, the 24 permutations correspond to a period of approximately 30 minutes if the permutation is of the order of 75 s.

In order to measure this concentration profile, an optical probe is located at least one fixed point of the circuit. Preferably, two optical probes are located on the recycling lines which connect the adsorbers downstream of the recycling pumps. The composition of the mixture is measured approximately once a second, and an average of 10 measurements are made in order to reduce the signal/noise ratio.

For each permutation with a period of 75 seconds, 7 vectors (i.e. approximately one every 10 seconds, corresponding to the mean of ten measurements) containing concentrations of ethylbenzene, para-xylene, meta-xylene, ortho-xylene and desorbent are stored in the memory. On the view screen, at the end of each phase (i.e. every 75 seconds, 3 curves giving the concentration of the species as a function of time are shown on the same graph: for example, PX, EB, MX+OX.

To control and regulate the process for SMB separation of an isomer from xylenes, the method thus comprises the following steps:

1) sending a light signal at a wavelength in the range 750 to 800 nm to at least one point of the unit;

2) capturing the Raman spectrum at the point under consideration;
3) processing the Raman spectrum using the matrix method discussed above;
4) capturing the value for the concentration of the species present at the end of this processing;
5) comparing the concentration value (or the concentration profile) obtained with a reference value (or a reference concentration profile);
6) acting, as a function of the difference between the measured value and the reference value on at least one actuating variable selected from the group formed by the internal flow rates, the feed flow rate, the desorbent flow rate, the extract flow rate, and the permutation period.

EXAMPLES

The two examples below are intended to illustrate the improvement in the measurement using the "absolute difference" variable when passing from prior art Example 1 to Example 2, in accordance with the invention.

Example 1

In Accordance with the Prior Art

In this example, the on-line measurement was carried out using a bypass loop with a measuring cell, a 532 nm laser source and a simplified method for utilizing spectra (not in accordance with the invention).

A Raman analyzer using a 532 nm laser exciter was used on a simulated moving bed xylene separation unit with para-diethylbenzene as the solvent to determine the concentrations of ortho (OX), meta- (MX), para-xylene (PX), ethylbenzene (EB) and para-diethylbenzene (PDEB).

To this end, a bypass loop with a measuring cell was installed which allowed a portion of the principal stream of the unit to be removed. The measuring cell comprised a sapphire window which could send the laser beam onto the sample and collect the Raman signal emitted thereby. Before entering the cell, the stream was thermostatted at 25° C., in order to record the spectra at this temperature. The Raman spectra collected were sent to the PC analyzer. The concentrations were obtained using the prior art method:

$$C_j = \frac{P_j \sigma_j}{\sum_{i=1}^{5} P_i \sigma_i} \quad (8)$$

In this formula, the values of $P_i$ and $\sigma_i$ are independent of the concentration of the various constituents. They were determined at 25° C. using only Raman spectra of the pure constituents and binary equimolar mixtures with the reference constituent ($\sigma_j = 1$).

Close to the bypass loop, a sampling point could remove an aliquot of the principal stream from the unit. This aliquot was used for a laboratory analysis by gas chromatography to determine the concentrations of the various constituents.

Gas chromatography (GC) is a proven method for analysis of C8-C10 hydrocarbons, providing reference values for the concentrations of the various constituents.

Thus, for 125 samples, the concentrations obtained using the Raman method were compared with those obtained using the GC reference method. A linear regression between the two series of measurements was carried out and characterized by a regression coefficient $R^2$.

The correlation between these two sets of values was also evaluated by the mean absolute difference, defined as:

$$\text{Mean absolute difference} = \frac{1}{n} \sum |y_{Raman} - y_{GC}|$$

where $y_{GC}$ are the concentrations obtained in GC, $y_{Raman}$ are those obtained in Raman spectroscopy and n is the number of concentrations measured. The maximum absolute difference was also recorded.

The results obtained are reported in Table 2. The correlation between the GC measurements and the Raman measurements was good (R2=0.9986). However, the Raman measurements had significant differences with the reference measurements: the mean absolute difference was 0.71% and the maximum difference reached 4.10%.

TABLE 2

Statistical correlation data between the relative concentrations (%) for GC and the Raman concentrations under the conditions of Example 1

| Compound | Linear regression coefficient ($R^2$) | Mean absolute difference (%) | Maximum absolute difference (%) | Range of concentration measurements (%) |
|---|---|---|---|---|
| PDEB | 0.9984 | 1.11 | 4.10 | 10-100 |
| OX | 0.9996 | 0.24 | 0.88 | 0-20 |
| MX | 0.9997 | 0.47 | 2.06 | 0-50 |
| PX | 0.9985 | 0.76 | 3.18 | 0-40 |
| EB | 0.9787 | 1.00 | 3.40 | 0-20 |
| Ensemble of constituents | 0.9986 | 0.72 | 4.10 | |

Example 2

In Accordance with the Invention

In this example, an on-line measurement was made using an immersing probe, a thermocouple in the vicinity of said probe, a 785 nm laser source and the spectrum utilization method presented in the invention.

Thus, this example was entirely in accordance with the invention.

A Raman analyzer using a 785 nm laser exciter was used on a xylene separation unit using para-diethylbenzene as the solvent, to determine the concentrations of ortho (OX), meta- (MX), para-xylene (PX), ethylbenzene (EB) and para-diethylbenzene (PDEB).

The Raman spectrum of the mixture was measured directly on the principal stream of the unit using an immersing probe. A thermocouple was installed close to the immersing probe.

The Raman spectrum and the temperature were measured at the same point of the unit and were thus sent simultaneously to the PC analyzer. The temperature of the sample, $T_{spl}$, at the measurement point was 175° C., which was different from the calibration temperature $T_{cal}$.

These data were exploited using the method described in the present invention, calibration being carried out using three different temperatures, namely 100° C., 140° C. and 180° C.

Cross comparisons with the GC reference method were carried out on a set of samples in a manner similar to that described in Example 1.

The results obtained are shown in Table 3.

The mean absolute difference was significantly reduced, changing from 0.72% in Example 1 to 0.19% in the present case.

This reduction in the mean difference was due to a large reduction in the maximum difference observed, which changed from 4.10% in Example 1 to 0.95% in this example.

The use of a 785 nm laser, which could minimize problems with fluorescent impurities, as well as the simultaneous measurement of the temperature, which could overcome problems due to temperature variations in the sample, are at the origin of the excellent agreement of the reference measurements with the Raman measurements.

TABLE 3

Statistical correlation data between the relative concentrations (%) for GC and the Raman concentrations under the conditions of Example 3

| Compound | Linear regression coefficient ($R^2$) | Mean absolute difference (%) | Maximum absolute difference (%) | Range of concentration measurements (%) |
|---|---|---|---|---|
| PDEB | 0.9996 | 0.23 | 0.84 | 10-100 |
| OX | 0.9998 | 0.15 | 0.50 | 0-20 |
| MX | 0.9999 | 0.18 | 0.58 | 0-50 |
| PX | 0.9992 | 0.12 | 0.42 | 0-40 |
| EB | 0.9994 | 0.29 | 0.95 | 0-20 |
| Ensemble of constituents | 0.9996 | 0.19 | 0.95 | |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application Ser. No. 09/01.108, filed Mar. 9, 2009, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for measuring the concentrations of species present at least one point of a separation unit functioning in simulated moving bed mode (SMB), using an immersing probe located at one point in the unit or on one of the streams entering or leaving said unit (termed the measuring point), and a thermocouple located in the vicinity of said measuring point, in order to capture the temperature ($T_{spl}$), in which method:

a) a monochromatic signal is sent through a first fibre optic connected to the immersing probe, originating from a laser source the wavelength of which is 785 nm plus or minus 1 nm;

b) a signal corresponding to the Raman effect, termed the Raman signal, is captured through a second fibre optic which is also connected to the immersing probe, and sent to a spectrometer using filters defining a cutoff threshold;

c) the Raman spectrum of the signal under consideration is recovered at the spectrometer outlet;

d) the Raman spectrum obtained is processed using a mathematical method which accommodates the temperature ($T_{spl}$) of the measuring point under consideration in order to obtain the concentration $C_j$ of the species present at said measuring point, said method for obtaining the concentrations $C_j$ of the various species present at the measuring point being based on the formula:

$$C_j = \frac{P_j(T_{spl}, C_1, \ldots, C_5)\sigma_j(T_{spl}, C_1, \ldots, C_5)}{\sum_{i=1}^{5} P_i(T_{spl}, C_1, \ldots, C_5)\sigma_i(T_{spl}, C_1, \ldots, C_5)}$$

in which:

$P_i$ is the integrated intensity of the Raman band due to molecule i; and $\sigma_i$ is the inverse of the relative effective cross section of the molecule i;

in which expression the integrated intensities $P_i$ are obtained from the measured intensities $M_j$ on the Raman spectrum by means of a matrix product in which the coefficients $a_{ij}$ of the matrix M result from a calibration carried out at the temperature ($T_{spl}$) of the measuring point, or at a plurality of temperatures framing said temperature of the measuring point, the inverse of the effective cross sections $\sigma_i$ being a function of the temperature ($T_{spl}$) and the concentrations ($C_i$) of the various constituents.

2. A measurement method according to claim 1, in which the total length of the first fibre optic and the second fibre optic is less than 1000 m, and preferably less than 700 m.

3. A measurement method according to claim 1, in which the or one of the measuring points when there are a plurality thereof is located at the recycling pumps on the eluent recycling circuit.

4. A measurement method according to claim 1, in which two measuring points are used located at the following positions: in the vicinity of the recycling pump on the eluent recycling circuit, and in the vicinity of the feed pump on the feed circuit.

5. A measurement method according to claim 1, in which three measuring points are used located at the following positions: the first point in the vicinity of the recycling pump on the eluent recycling circuit; the second point in the vicinity of the feed pump on the feed circuit; and the third measuring point in the rectification zone of the raffinate distillation column.

6. Application of the measurement method according to claim 1 to the control and regulation of a simulated moving bed xylenes separation unit, the difference between a concentration profile measured using said method and a reference concentration profile for at least one of the constituents present in the unit allowing at least one control parameter selected from the group constituted by the following to be adjusted: internal flow rates, feed flow rate, eluent flow rate, extract flow rate, and permutation period.

* * * * *